United States Patent [19]

Carter

[11] Patent Number: 4,755,043

[45] Date of Patent: Jul. 5, 1988

[54] PORTABLE SCANNING DIGITAL PUPILLOMETER AND METHOD OF USE THEREOF

[75] Inventor: Elbert P. Carter, Wilmington, Del.

[73] Assignee: Somec, Inc., Wilmington, Del.

[21] Appl. No.: 797,769

[22] Filed: Nov. 14, 1985

Related U.S. Application Data

[63] Continuation-in-part of Ser. No. 701,994, Feb. 15, 1985, abandoned.

[51] Int. Cl.$^4$ ............................................... A61B 3/10
[52] U.S. Cl. .................................. 351/205; 351/211; 351/221
[58] Field of Search ...................... 351/205, 211, 221; 356/378, 379, 380, 384

[56] References Cited

U.S. PATENT DOCUMENTS 3,966,310  6/1976  Larson .

OTHER PUBLICATIONS

Watanabe, "A Solid-State Television Pupillometer",-1982, Vision Research, vol. 22, pp. 499-505.
Jones et al., "A New Solid State Dynamic Pupillometer Using a Self Scanning Photo-Diode Array",-1983, Institute of Physics.

Primary Examiner—Rodney B. Bovernick

[57] ABSTRACT

A portable, hand-held, dynamic, automatic scanning, measuring and recording device capable of inspecting holes and measuring gaps in any animate or inanimate object of up to about 10 millimeters in size (diameter, for example) such as a pupil of a vertebrate eye or a printed circuit board. The device comprises a light weight viewing optics/image sensor and a microprocessor controlled automatic scanning and data capture/storage system with a digital readout of pupil diameter measurements.

2 Claims, 4 Drawing Sheets

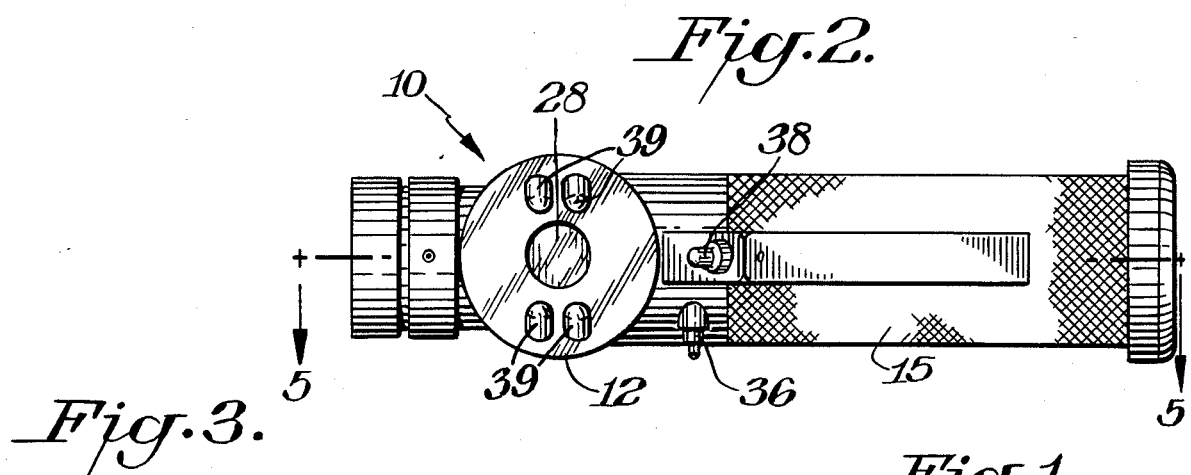
Fig. 2.
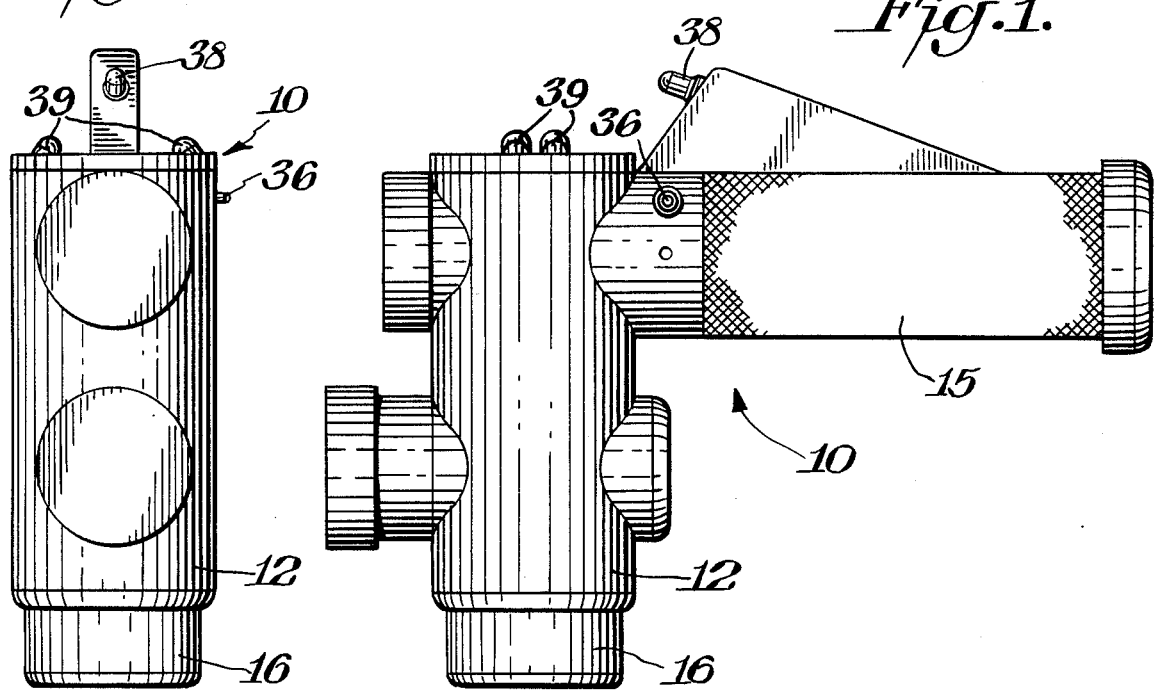
Fig. 3.
Fig. 1.
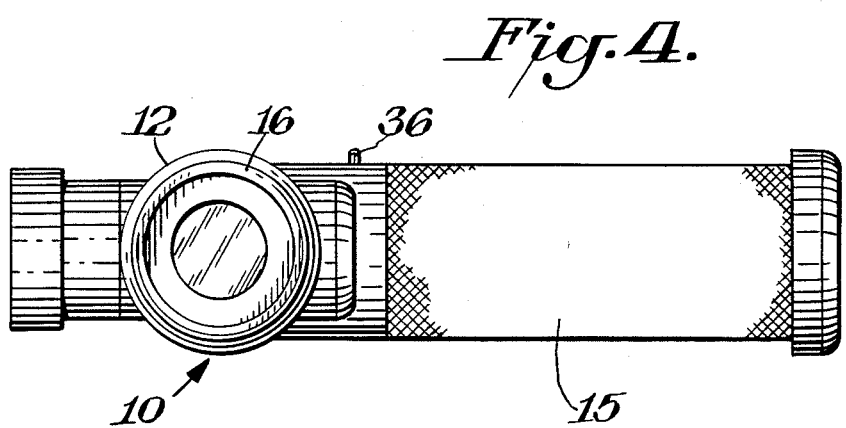
Fig. 4.

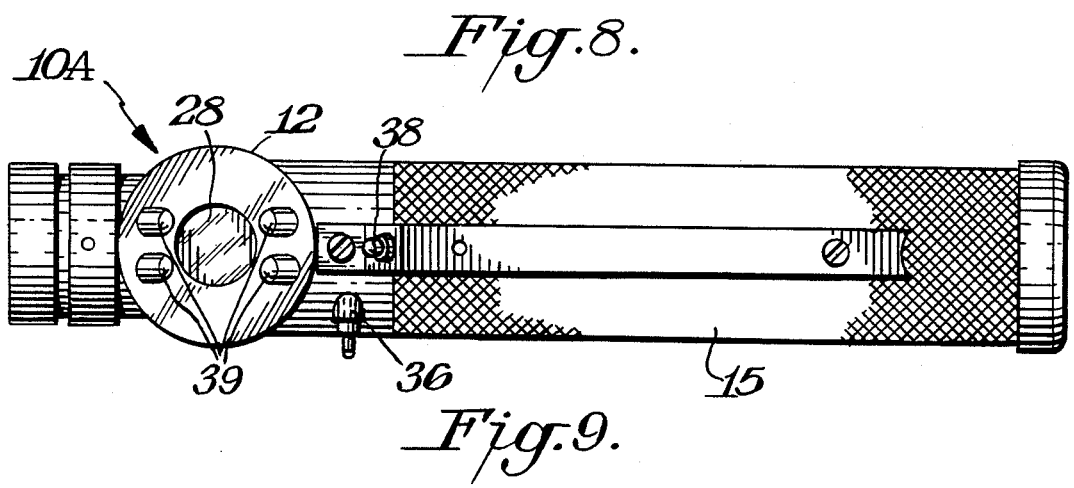
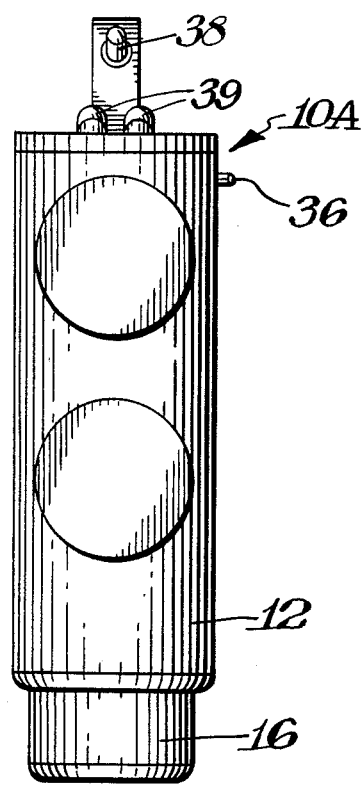

PORTABLE SCANNING DIGITAL PUPILLOMETER AND METHOD OF USE THEREOF

This application is a continuation-in-part of application Ser. No. 06/701,994 filed Feb. 15, 1985 now abandoned.

BACKGROUND OF THE INVENTION

This invention relates to a hand-held, scanning, measuring and recording device useful in the inspection of holes and measurements of gaps of up to about 10 millimeters in diameter and is particularly useful in pupillometry.

Numerous objective methods have been devised for the measurement and recording of the size of the pupil of the human eye as well as of laboratory animals, since pupil size is an important indicator of autonomic nervous system activity and the general physiological state of the subject. These methods have provided quantitative information for monitoring the duration of action of drugs which produce a miotic or mydriatic effect and have been beneficial to anesthesiologists and others in the operating room, intensive care units, and recovery rooms.

However, for many applications, especially in clinical investigations and basic research, a measure of the dynamic response of the pupil to a light stimulus, i.e. light reflex, is required. Included among dynamic pupillometric systems which have been developed for human study are infrared (IR) cinematography (Lowenstein, U.S. Pat. No. 3,533,683), IR spot scanning or IR video pupillography. All of these methods require elaborate, expensive and bulky equipment and are not well suited for use in operating rooms and other confined areas. Additionally, these prior art methods and apparatus require considerable set-up time, high initial cost, subject training and skilled maintenance.

SUMMARY OF THE INVENTION

The present invention overcomes the problems described above and satisfies the requirements for a light weight, low cost digital pupillometer by providing an instrument which utilizes two main components, namely, a hand-held optical unit and a commercially available microprocessor based control and data processing unit, combined in a package which is readily adapted for use by a physician or those engaged in advanced animal research and clinical investigations.

Broadly speaking, the apparatus of the present invention is for measuring hole diameter, especially pupil diameter and changes in pupil diameter in response to an excitation light pulse. It is intended primarily for use by doctors, especially anesthesiologists as one indicator of the level of anesthetization of patients on the operating table, and researchers in the bioassay of various psychopharmacologic compounds, in the assessment of narcotic dependency, and in the analysis of drugs that have a local effect on the iris. The apparatus can be used to measure pupil diameter under a variety of conditions limited only by the ability of the operator to center the pupil image on the image sensor. It can be adapted to measure a linear dimension of any appropriately lighted object whose image can be so positioned, provided the hole diameter does not exceed 10 millimeters.

The apparatus of this invention comprises a hand-held, light weight optics/image sensor and a microprocessor based control and data processing unit. The main tube of the optical unit projects an image of the eye on a reticle marked with concentric circles. It is viewed by an operator through an eyepiece, providing the means for the operator to focus and center the pupil image. A handle perpendicular to the main tube houses the image sensor. An optical beam splitter directs the reflected near infra-red light, provided by i-r emitting diodes, from the object being observed toward the image sensor. A lens in that path projects an image of the eye onto the sensor at about one-third size. A set of infra-red emitting diodes (IREDs) are positioned to irradiate the pupil/iris area providing the radiation for that image. A lamp for background illumination (the "viewing" lamp) and one for the pulsed excitation are provided along with a "trigger" switch to initiate a series of measurements.

The microprocessor "base" unit houses the computer, the battery power source, a 4×4 keypad and a display unit with two 16-character lines. It controls the viewing lamp, pulses the excitation lamp, and sequences the series of image captures at ten per second. It calculates the pupil diameter for each capture and displays the results. The resulting data is stored and means to output to a printer is provided.

My invention further comprises a method for the study of pupillary effects on humans and laboratory animals which comprises the steps of irradiating the eye in the area of the iris and pupil with (non-visible) infra-red (non-visible) radiation, and selectively directing light from a (visible) light source to the area of the pupil to excite pupillary reactions.

The novel features and operation of the present invention will be better understood from the discussion and explanation of the disclosed embodiment taken together with the accompanying drawings.

BRIEF DESCRIPTION OF THE DRAWINGS

FIG. 1 is a top plan view of a pupillometer which embodies and is constructed with the present invention;

FIG. 2 is a front-elevational view of the pupillometer shown in FIG. 1;

FIG. 3 is a side-elevational view;

FIG. 4 is a rear elevational view;

FIG. 8 is another front-elevational view of the pupillometer shown in FIG. 1;

FIG. 9 is another side elevational view.

DESCRIPTION OF THE PREFERRED EMBODIMENT

Reference will now be made in detail to the present preferred embodiment of the invention, an example of which is illustrated in the accompanying drawings.

Figure 5:
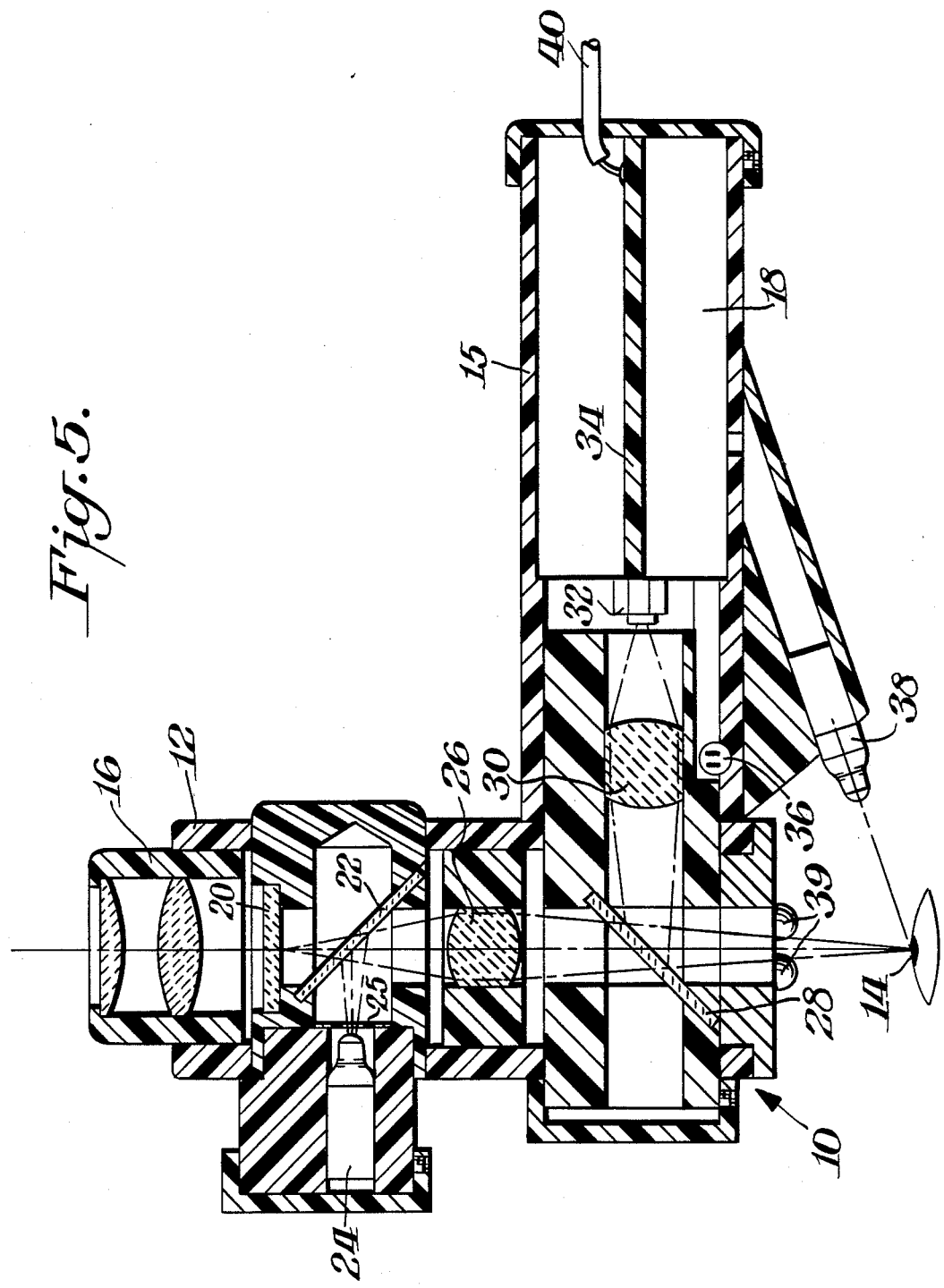
FIG. 5 is a cross-sectional view taken through FIG. 2 along line 5—5.
Figure 6:
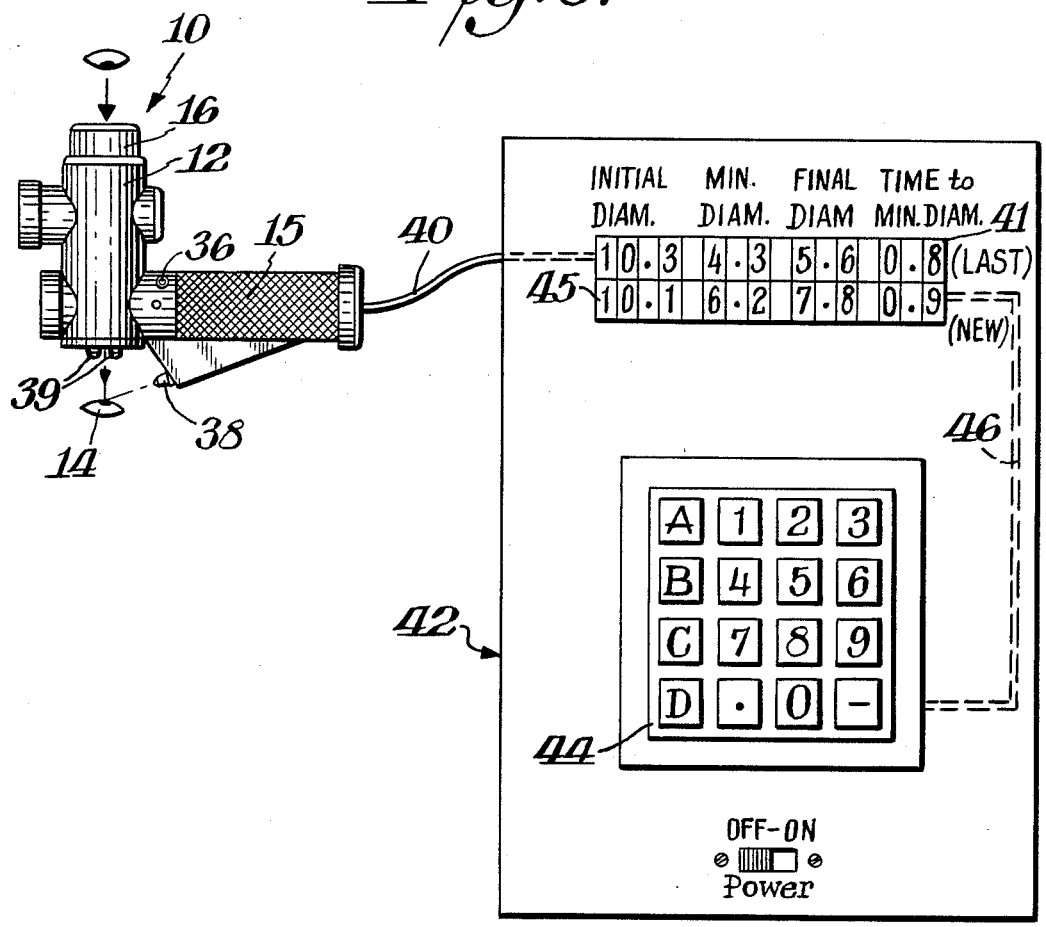
FIG. 6 is a view of the control and display panel.

The preferred embodiment is seen to include a hand-held pupillometer comprising an optical unit (10), shown in FIG. 1 and a microprocessor based control and data processing unit (42), shown in FIG. 6. The main tube (12) of the optical unit projects an image of patient's eye (14) on a reticle (20). The screen which is viewed by an operator through an eyepiece (16) is marked with concentric circles. The image sensor (32) and associated circuit board (34) which is housed (18) in a handle (15) perpendicular to the main tube is a 64K dynamic RAM memory chip with a glass lid (IS32 OpticRAM) which is commercially available from Micron Technology, Inc. of Boise, Id. The OpticRAM is composed of 65,536 individual image sensing elements called pixels. These pixels are organized into two rectangles of 128×256 pixels each. They can be used as one 256×256 array of pixels. The pixels can only be used to indicate light or dark. During the scan each pixel capacitance is charged to the power supply voltage. Between scans the light falling on each pixel discharges that capacitance. If the voltage on a particular pixel capacitance is discharged below a presettable level, that pixel will be read out as light (white) on the next scan; otherwise the pixel will indicate dark (black). The contrast between the iris and the pupil is quite adequate for the light-dark discrimination between the iris and the pupil edge. A complete scan can be taken every tenth of a second.

The IS32 OpticRAM involves an arrangement of pixels in a geometrical matrix of 256 rows and 256 columns with the rows stretched to 512 element positions. The high speed scanner scans the 256 column positions for each row in sequence. The data bits are transmitted serially to the microprocessor unit at a 3 MHz rate. These are assembled into 8-bit bytes and stored in an 8K×8 bit static RAM chip. The full scan takes about 22 milliseconds. A new scan is started 78 milliseconds later. The pupil image for each row ideally is just a continuous string of dark bits, the number of which is easy to determine. The row with the most dark bits would correspond to the desired diameter. However, with the inevitable noise, the bits for several adjacent rows are examined and the most probable pixel count selected. With known optical reduction ratio and pixel spacing the diameter can be calculated using that count.

The high speed hardware scanner system for the IS32 OpticRAM is packaged to mount in the handle of the optical unit (15). Since reading a dynamic RAM bit is a four step process, a 12 MHz. clock is required to achieve a 3 MHz. bit rate. For this reason it is highly desirable to have the scanner physically near the sensor. In addition to the data bits, the scanner sends a synchronous signal through connecting cable (40) to tell the microprocessor when each bit is there and another at the end of each group of eight data bits.

The irradiation for pupil measurement is adjusted for iris-pupil contrast. It is understood that if the level of irradiation is too low some of the pixels in the iris area will remain dark, giving a mottled effect. If the level is too high, pixels in the pupil area will indicate light. The mottled effect is easy to detect in the image and the radiation level can be increased until it disappears. As the radiation level is increased beyond a point, the observed diameter will be constant or diminish slightly until the level at which pupil area pixels start to indicate light. This radiation level is preset ordinarily. However, it can be made manually or automatically adjustable for special applications.

The viewing lamp(38) provides illumination for the operator to position and focus the image of the eye properly. The viewing lamp is located to minimize any excitation of pupillary response; however its intensity must be kept as low as is practical. In some cases it will be turned off to prevent any pupil response interaction.

The microprocessor based control and data processing unit of my invention comprises a Motorola 68092E, program ROM (EPROM-2764, 8K bytes), RAM (2 HM6264, 8K bytes each, static), a LCD with two 16 character lines (41) (45), a 4×4 array keypad (44), a 24 hour clock, a viewing lamp control to provide 8 steps from half to full normal voltage with shut-off for manual or automatic selection and an exciter lamp on/off control. The exciter lamp level is normally preset to a predetermined intensity measured with a standard radiometer. The unit is powered by a 6 volt battery, 4.5 AH, GEL-CEL, with a 5.0 volt regulator and built in current limiting, constant-voltage charging regulator.

The keypad (44) shown in FIG. 6 is the means by which the operator sets up and controls the operation of the pupillometer of this invention. The keypad is connected to the digital display (45) by cable (46). The control is achieved by entering a series of two character commands, each consisting of a letter followed by a digit. When data are needed from the operator, prompts will come up on the display naming the items needed. The operations divide into three main groups - set-up, measure, and recall/print data.

At power turn-on the date/time data is displayed. If it needs to be corrected the "Set-time" command, say "C2," is entered. Prompts for the month/day and hour/minute follow. After the new data are entered the display clears and prompt for the next command follows. A "Display-time" command, say, "C1," returns the new date-time data to the display, up-dated to current time.

One of the two 8k byte static RAM units is used to store the image data from the sensor. The other provides storage for the patient data and for program execution. The patient data will be placed starting at the low address end of the unit. A relatively small amount of RAM at the high address end will be used for the program. That area is protected from patient data. At the start of a series of measurements the patient data area is cleared of previous such data. Since the clock and RAM units are powered continuously, the patient data from one series is retained until it is erased. If it is not, the new patient data is entered following the old. The memory test command will clear and test both the image and patient data areas.

The set-up patient ID command will prompt for a memory clear if that has not been done and automatically enter the date-time into the patient data record and ask for a patient ID number. After that number has been entered, a prompt for a viewing lamp level follows. For a manual set of that level, a number from 1 to 7 should be entered. 1 to 7 numbers provide eight lamp voltages from half to full voltage rating. The next prompt is for the exciter lamp pulse duration in tenths of a second. The viewing lamp level number and the exciter lamp duration selected are entered in the patient record. At this point the two-character "measure" command must be entered.

Figure 7:
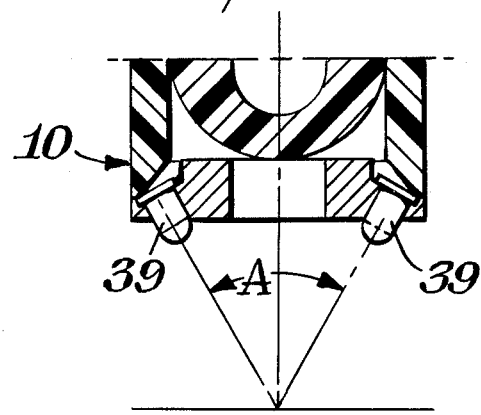
FIG. 7 is a cross-sectional view showing a mounting arrangement for the infra-red emitting diodes.

Measurements are made by positioning the optical unit over the patient's eye (14) focusing and centering the iris/pupil image on the reticle-screen (10) with the push bottom switch (36) actuated. Scanning the sensor (32) starts when the switch is released and the processor attempts to extract a diameter from each scan. When a well focused image is present on the sensor and good diameters are obtained, that diameter is entered as the initial diameter for that set of readings. The exciter lamp (24) is pulsed, its radiation passes through an aperture (25); is reflected from the beam splitter (22); passes through the focusing lens (26) then through a second beam splitter (28) to focus on the pupil. The dynamic pupil reaction is obtained every 0.1 sec. and accumulated for 3.0 to 5.0 sec. timed from the start of the exciter lamp pulse. The ir emitting diodes (39) supply light for reflection from the pupil which reflected light passes through the focusing lens (30) onto the detector (32). The ir diodes are arranged at the included angle shown as Angle A in FIG. 7.

A preferred orientation of the i-r diodes (39) in optical unit 10A for making measurements from reflective surfaces is shown in FIGS. 8 and 9. The diameters entered in the patient's record will be the number of dark pixels representing each diameter. That number will be less than 255 and can be stored in a single byte. While the series of 30 scans (every 3 seconds) are being made, the processor will be looking for the minimum diameter and may be programmed to halt the series then. When the series is terminated, the processor will calculate and display the initial diameter, the minimum diameter, and the diameter after 3 seconds. Those data will be displayed for the last and next to the last series of measurements.

The results of earlier measurements can be displayed, either backing up one series at a time, or starting with the first series of the set and stepping forward. The processor will calculate the diameter data from the pixel data and display it as described above. If desired, the apparatus of my invention can include a printer so that the entire patient record can be printed out in any desired form. The pixel data may be used to plot response curves. The diameter data can be calculated as defined above and printed.

A preferred embodiment of a pupillometer of this invention has been described which has general application in anesthesiology, as well as in both research and clinical environments. It will be readily appreciated, by those skilled in the art, that a number of modifications are possible for the purpose of optimizing the performance of a particular pupillometer for a particular experiment or measurement.

The present invention affords a convenient and accurate means of accumulating data which, when analyzed and properly interpreted, provides an indication of a variety of neurophysiological conditions even when they are in an incipient stage.

It will be apparent to those skilled in the art that various additions, substitutions, modifications, and omissions can be made to the present invention without departing from the scope or spirit of the invention. Thus, it is intended that the present invention covers such, provided that they come within the scope of the appended claims and their equivalents.

What is claimed is:

1. A portable scanning digital pupillometer which comprises a body size to be hand-held;
    two light sources mounted on said body and positioned to direct light therefrom to an eye in the area of the pupil upon hand-positioning of the body, one light source emitting a light beam impinging on said eye along a line within the limits of 0° to 9° from a plane tangent to the center of the pupil, and another light source emitting a beam impinging on said eye in the vicinity of said pupil more directly into said pupil that said other beam;
    means for selectively actuating the light source impinging more directly on the pupil so that the responsive action of the pupil to said application of the light from said light source can be observed and recorded;
    means for irradiating an eye with near infra-red radiation and directing that radiation from the eye being observed to a bilevel pixel image sensor;
    a bilevel pixel image sensor; and
    a microprocessor based control and data processing unit comprising a computer, a battery power source, a keypad, and a display unit.

2. A method for dynamically measuring the size and change in size of an eye pupil which comprises the steps of applying radiation to an eye in the area of the pupil from an infra-red radiation source to provide an image of the eye on a bilevel pixel array image sensor,
    selectively directing light from another source to the area of the pupil,
    positioning the optical unit of the puillometer of claim 2 over the eye,
    focusing and centering the iris/pupil image on a reticle-screen,
    scanning bilevel pixel array image sensor, transferring and storing a digital representation of the image of the pupil by means of a microprocessor, calculating, by means of said microprocessor, the pupil diameter for each said representation, and displaying the results of said calculations.

* * * * *